US00PP35197P2

(12) United States Plant Patent
VandenLangenberg et al.

(10) Patent No.: US PP35,197 P2
(45) Date of Patent: May 30, 2023

(54) STRAWBERRY PLANT NAMED 'CBC005'

(50) Latin Name: ***Fragaria* x *ananassa***
Varietal Denomination: CBC005

(71) Applicant: California Berry Cultivars, LLC, French Camp, CA (US)

(72) Inventors: Kyle M VandenLangenberg, Tracy, CA (US); Douglas V Shaw, Davis, CA (US)

(73) Assignee: California Berry Cultivars, LLC, French Camp, CA (US)

( * ) Notice: Subject to any disclaimer, the term of this patent is extended or adjusted under 35 U.S.C. 154(b) by 0 days.

(21) Appl. No.: 17/951,586

(22) Filed: Sep. 23, 2022

(51) Int. Cl.
*A01H 5/08* (2018.01)
*A01H 6/74* (2018.01)

(52) U.S. Cl.
USPC ..... Plt./208
CPC ..... *A01H 6/7409* (2018.05); *A01H 6/74* (2018.05)

(58) Field of Classification Search
USPC ..... Plt./208, 209
CPC ..... A01H 5/0893
See application file for complete search history.

(56) References Cited

U.S. PATENT DOCUMENTS

| | | | | |
|---|---|---|---|---|
| PP19,975 | P2 | 5/2009 | Shaw et al. | |
| PP20,363 | P2 | 9/2009 | Chandler | |
| PP22,542 | P3 | 3/2012 | Shaw et al. | |
| PP26,709 | P3 | 5/2016 | Larson et al. | |
| PP34,684 | P2 * | 10/2022 | Suiker | Plt./208 |

OTHER PUBLICATIONS https://issuu-com.translate.goog/revistamercados/docs/mercados_159/s/15139803?_x_tr_sl=es&_x_tr_tl=en&_x_tr_hl=en&_x_tr_pto=sc; Mar. 2022; 3 pages.*
Mercados Newsletter, Apr. 19, 2022, 3 pages https://revistamercados.com/eurosemillas-debemos-desarrollar-variedades-sostenibles-y-viables-economicamente/.
Mercados Newsletter, Aug. 26, 2022, 3 pages https://revistamercados.com/adelanto-y-cbc015-las-nuevas-variedades-de-fresa/.

* cited by examiner

*Primary Examiner* — Kent L Bell
(74) *Attorney, Agent, or Firm* — Phase M Legal

(57) ABSTRACT

A new and distinct cultivar of strawberry plant (*Fragaria* x *ananassa*) named 'CBC005' is presented here. This new short-day strawberry cultivar is characterized by moderate vigor plants which produce exceptionally large early yields of attractive conical to blocky fruit. In addition, plants of 'CBC005' are resistant to *Macrophomina phaseolina.*

5 Drawing Sheets

Latin name of the genus and species of the plant claimed: Botanical classification: *Fragaria* x *ananassa.*

Variety denomination: The new strawberry variety denomination is 'CBC005'.

BACKGROUND OF THE INVENTION

This invention relates to a new and distinctive short-day type cultivar designated as 'CBC005'. The new cultivar was the result of a controlled cross performed in 2015 in Huelva, Spain between the cultivar 'Benicia' (U.S. Plant Pat. No. 22,542) and the cultivar 'Florida Radiance' (U.S. Plant Pat. No. 20,363). 'CBC005' was first fruited at an experimental orchard near Oxnard, Calif. in 2016, where it was selected, originally designated 115.054-601, and propagated asexually by runners. Following selection and during testing, the plant of this selection was later designated 'CBC005'. Asexual propagules from this original source have been tested in Watsonville, Calif., in Oxnard, Calif., and to a limited extent in grower fields starting in 2020. The cultivar is stable and reproduces true to type in successive generations of asexual reproduction.

Comparison with Parents

The parent 'Benicia', is a short-day cultivar that was selected for its overall high appearance score and large, firm fruit. Plants of 'Benicia' are larger than 'CBC005'. The parent 'Florida Radiance' is a short-day cultivar that was selected for its high early season yield. Plants of 'Florida Radiance' are similar in size to 'CBC005' but appear less vigorous when grown in typical commercial settings.

SUMMARY OF THE INVENTION

'CBC005' is a short-day cultivar that produces fruit over an extended period when treated appropriately in arid, sub-tropical climates. When treated with appropriate planting regimes, 'CBC005' has larger fruit and produces individual-plant yields greater than that of either parent. The following traits have been repeatedly observed over multiple testing years and locations and are determined to be unique characteristics of 'CBC005'. These characteristics in combination distinguish 'CBC005' as a new and distinct Strawberry plant:

1. Medium sized plant with open habit in the early season.
2. Rapid plant growth rate early followed by stable size once fruit set begins.
3. Extremely early flowering habit result in large early yields.
4. Extremely early fruiting.
5. Large fruit that ranges from conical to blocky.
6. Fruit is firm throughout the growing season.

7. Fruit postharvest longevity is good.
8. Excellent freezer crop.

'The cultivar 'CBC005', when planted under appropriate conditions, is an extremely early fruiting short-day cultivar with exceptionally high early and total yields. Early yield is of increased interest to fresh market strawberry sales companies as return prices on fruit volume are substantially higher. In addition to its early yield performance, 'CBC005' is resistant to *Macrophomina phaseolina*, the causal agent of charcoal rot.

BRIEF DESCRIPTION OF THE FIGURES

The accompanying color photographs, identified as FIGS. 1 through 5, show the appearance of typical specimens of the new strawberry cultivar designated 'CBC005'. These Figures depict the colors, as nearly true as it is reasonably possible given differences in color illustrations of this character. Accordingly, color in the photographs may differ slightly from the colors discussed in the botanical description.

DETAILED BOTANICAL DESCRIPTION OF THE PLANT

Figure 1:
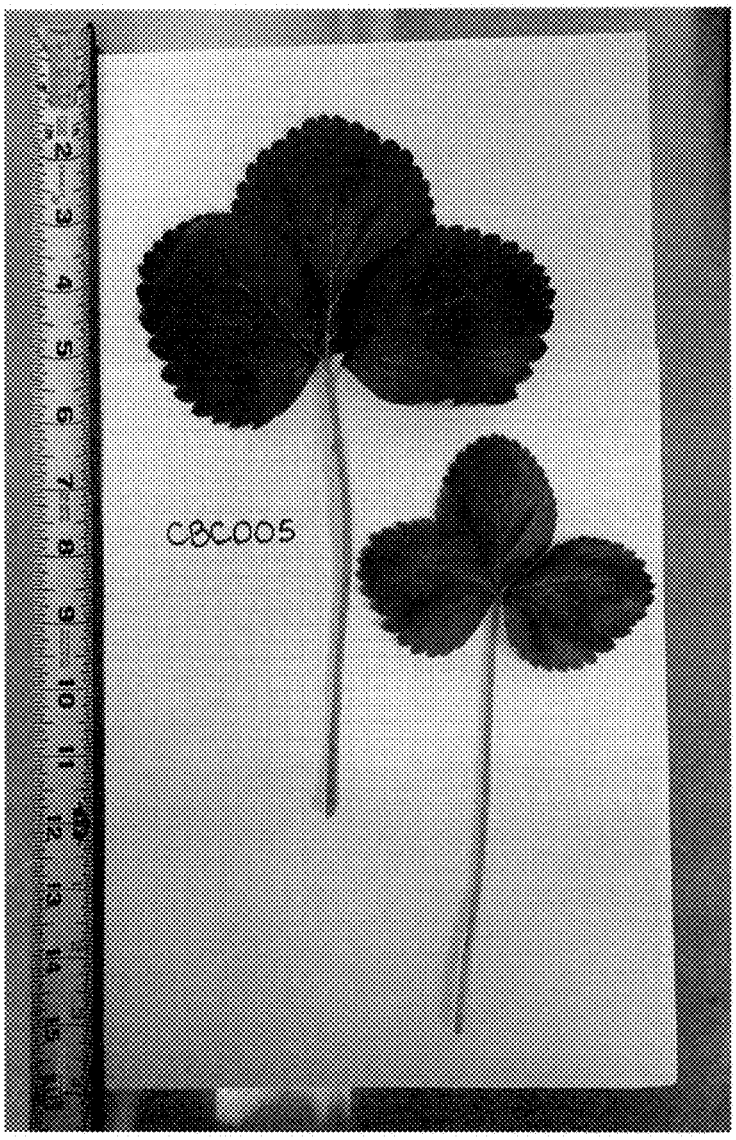
FIG. 1 shows a typical leaf and petiole structure.
Figure 2:
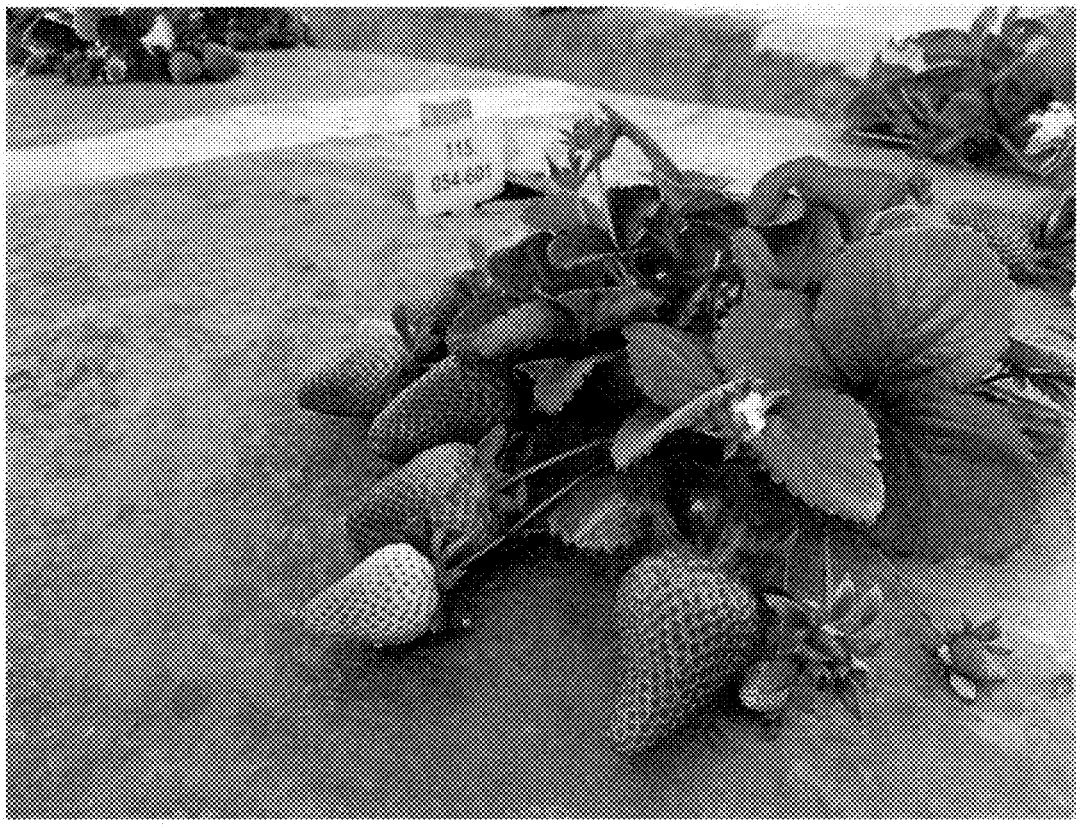
FIG. 2 shows a typical plant and fruit early season.
Figure 3:
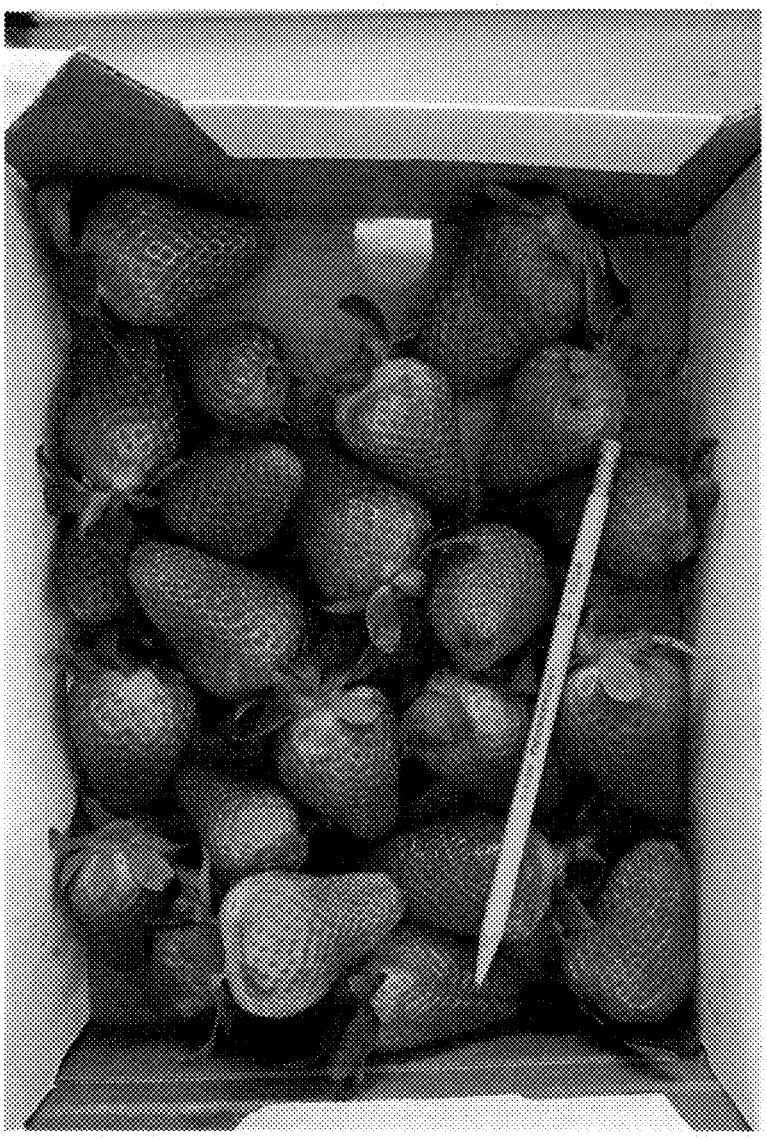
FIG. 3 shows typical fruit in a box early season.
Figure 4:
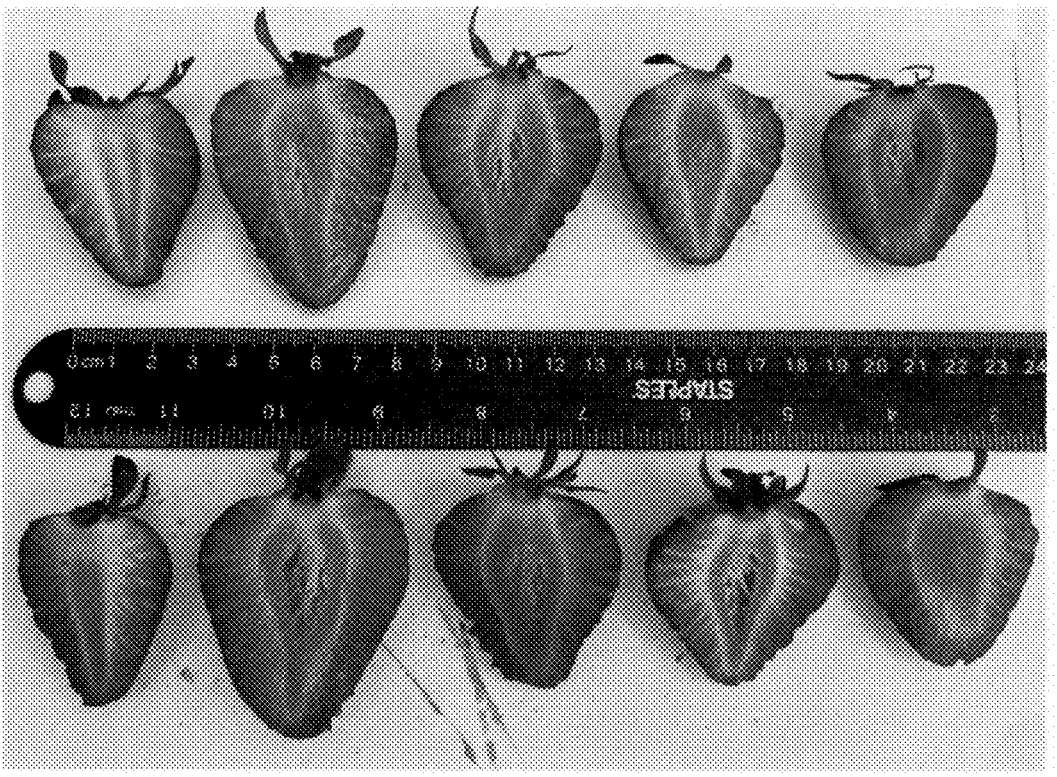
FIG. 4 shows a cross-section of representative fruit mid-season.
Figure 5:
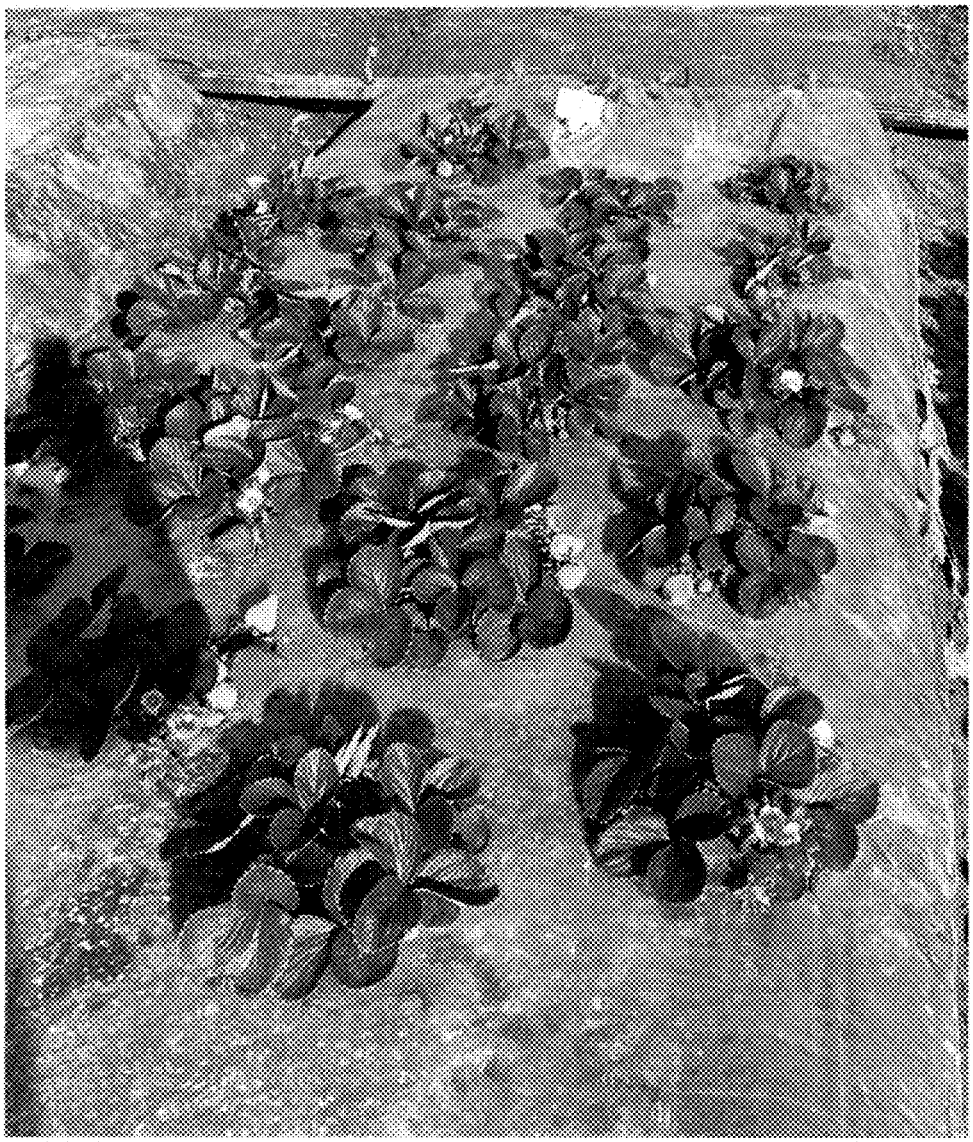
FIG. 5 shows a typical plot in the field of plants and fruit.

'CBC005' is a new and distinct short-day cultivar of strawberry, genus and species *Fragaria* x *ananassa*. Plants of 'CBC005' do not bloom continuously in higher elevation plantings, and do not bloom in the heat of low elevation nursery locations such as French Camp, Calif., consistent with other short-day varieties. The plants of the new cultivar have a moderate vigor and produce multiple crowns during the growing season. 'CBC005' exhibits several characteristics which are improvements over one or both of its parent varieties, and other cultivars known to the Inventors. These characteristics are compared with other cultivars in Table 2, 3, and 4.

The fruit size of 'CBC005' is moderately large, with a seasonal average of 34.7 g, slightly larger than its parents. The fruit size of 'CBC005' is ideal since it is not too large to be damaged in shipping containers, but not too small to allow for efficient picking and packing. The 'CBC005' fruit also hangs down on the shoulder of the bed later in the season, which makes for greater visibility and ease of picking. Storability of the fruit has not been measured but in informal observations the fruit retains good physical characteristics and appearance for several days after harvest at room temperature and up to at least a week in common refrigerator conditions of roughly 3° C.

'CBC005' produces mostly long conic fruit like its parent 'Benicia', while the fruit of 'Florida Radiance' is a longer torpedo shape, and often suffers multiple defects. The fruit of 'CBC005' generally ripens evenly from the tip to the shoulders of the berry, resulting in a uniform red color over the whole fruit. In contrast, the fruit of 'Florida Radiance' has a more pronounced tip to top ripening pattern that can often result in a pronounced white-shoulder. The fruit of 'CBC005' can be more blocky than conical early in the season and has a firmness equal to or greater than its two parents.

The data set for 'CBC005' set forth below was collected in May 2022 from plants grown at a test plot in Oxnard, Calif. Yield, size, and firmness data is either averaged over the entire 2021-2022 growing season or presented as monthly totals at the same location. Description data was collected on five-month-old plants.

The observed characteristics of 'CBC005' are set forth in Table 1, 2, 3, and 4 below. Color terminology where noted is in accordance with Panton Color Formula Guide GP1601A. The observed characteristics of 'CBC005' are also compared to known cultivars 'Fronteras' (U.S. Plant Pat. No. 26,709) and 'San Andreas' (U.S. Plant Pat. No. 19,975) in Table 2, 3, and 4. Table 5 sets forth the test results of DNA fingerprinting using eight SSR markers.

Table 1: Detailed Description of Characteristics of 'CBC005"

Specification:
- *Genus/species.*—*Fragaria* X *ananassa.*
- *Market name.*—Strawberry.

Parents:
- *Female.*—'Benicia'.
- *Male.*—'Florida Radiance'.

Plant:
- *Type.*—Short-day, non-everbearing.
- *Growth habit.*—Semi-upright.
- *Foliage density.*—Moderate.
- *Vigor.*—Moderate.
- *Height.*—Average 13 cm; range 11.5-15.5 cm.
- *Width.*—Average 26 cm; range 21-29 cm.
- *Disease tolerance.*—Test plots have shown tolerance to *Macrophomina phaseolina.*
- *Disease susceptibility.*—Susceptible to *Phytophthora cactorum.*

Leaf:
- *Width.*—9 cm.
- *Color.*—Adaxial surface: Pantone 2266 U. Abaxial surface: Pantone 2263 U.
- *Pubescence.*—Slight density.
- *Glossiness.*—Medium.
- *Variegation.*—Not present.

Terminal leaflet:
- *Length.*—57 mm.
- *Width.*—47 mm.
- *Ratio* (*length/width*).—1.2.
- *Margins.*—Crenate to serrate.
- *Leaflet shape.*—Obovate.
- *Base shape.*—Cuneate.
- *Cross-section shape.*—Concave.

Petiole:
- *Pubescence.*—Slight density.
- *Petiole color.*—Pantone 2289 U.
- *Petiole length.*—Average 5.8 cm; range 5-6.8 cm.
- *Petiole diameter.*—Average 1.5 mm; range 1-2 mm.

Stipule:
- *Anthocyanin coloration.*—Light.
- *Length.*—Average 14 mm; range 10-16 mm.
- *Width.*—Average 5 mm, range 4-6 mm.

Inflorescence:
- *Flowering time.*—Extremely early (2-4 weeks before parents).

*Position*.—Mostly at or above canopy.
*Petal arrangement*.—Slightly overlapping.
*Calyx size*.—Larger than corolla.
*Number of blooms*.—5.
*Length*.—3.5 cm.
*Flower diameter*.—Average 36 mm; range 24-43 mm.
*Petal number*.—Average 5.5; range 5-6.
*Petal length*.—Average 16.8 mm; range 13.7-19.7 mm.
*Petal width*.—Average 12.8 mm; range 10.8-14.8 mm.
*Petal color*.—Adaxial surface Pantone 11-0601. Abaxial surface Pantone 11-4300.
*Ratio* (*length/width*).—1.3.
*Calyx color*.—Adaxial surface: Pantone 7483 U. Abaxial surface: Pantone 2263 U.
*Stamens length*.—Average 29 mm; range 23-31 mm.

Pedicel:

*Pubescence*.—Slight density.
*Length*.—128 mm.
*Width*.—1.5 mm.
*Ratio* (*length/width*).—85.
*Color*.—Pantone 2289 U.

Fruit:

*Bearing*.—Short-day, non-everbearing.
*Harvest season*.—November to June in Oxnard, Calif.
*Time to maturity*.—Approximately 4 weeks after flowering.
*Length*.—52 mm-63 mm (avg 57.5 mm).
*Width*.—38 mm-47 mm (avg 43 mm).
*Flavor*.—Sweet and slightly acidic.
*Individual fruit weight*.—Seasonal average: 34.7 g.
*Shape*.—Mostly conic, some blocky.
*Achenes*.—Just below fruit surface.
*Glossiness*.—Medium/high.
*External color evenness*.—Even.
*External color*.—Pantone 7628 U.
*Internal color*.—Pantone 3516 U.
*Band at top without achenes*.—Narrow width.
*Fruit yield*.—Grams per plant: 1511 g.
*Firmness*.—0.63 kg/force.
*Achene color*.—Pantone 2288 U.

Under standard fall plantings in Southern California, with typical planting dates of October 1$^{st}$, 'CBC005' begins producing marketable fruit typically between December 1$^{st}$ and December 15$^{th}$. By comparison, variety 'Fronteras' on the same planting date is substantially later, with marketable fruit production typically beginning after January 15$^{th}$.

TABLE 2

Marketable yield of 'CBC005' compared to other known cultivars in Oxnard, CA during the 2021-2022 season.

| | Marketable yield (g/plant) | | | | | |
|---|---|---|---|---|---|---|
| Cultivar | December | January | February | March | April | Total |
| 'Fronteras' | 0 | 78 | 130 | 366 | 493 | 1068 |
| 'San Andreas' | 88 | 91 | 118 | 402 | 393 | 1093 |
| 'CBC005' | 115 | 133 | 197 | 533 | 532 | 1511 |

TABLE 3

Size of 'CBC005' compared to other known cultivars in Oxnard, CA during the 2021-2022 season.

| | Fruit size (g/fruit) | | | | | Aver- |
|---|---|---|---|---|---|---|
| Cultivar | December | January | February | March | April | age |
| 'Fronteras' | 49.0 | 45.4 | 43.8 | 30.6 | 24.7 | 35.5 |
| 'San Andreas' | 35.9 | 31.1 | 33.8 | 29.4 | 24.6 | 29.8 |
| 'CBC005' | 44.6 | 35.3 | 40.6 | 35.5 | 26.5 | 34.7 |

TABLE 4

Firmness of 'CBC005' compared to other known cultivars in Oxnard, CA during the 2021-2022 season.

| | Firmness (kg/force) | | |
|---|---|---|---|
| Cultivar | March | April | Average |
| 'Fronteras' | 0.49 | 0.51 | 0.50 |
| 'San Andreas' | 0.60 | 0.62 | 0.61 |
| 'CBC005' | 0.64 | 0.60 | 0.62 |

TABLE 5

DNA finger printing results of eight SSR markers.

| | Allelic Fingerprint Analysis | | | | | | | |
|---|---|---|---|---|---|---|---|---|
| Cultivar | M1 | M2 | M3 | M4 | M5 | M6 | M7 | M8 |
| 'CBC005' | 212, 224, 229 | 259, 264, 269, 271, 275 | 190, 232 | 279, 289 | 154, 156 | 242, 257, 261 | 121, 130 | 215, 222, 228 |

We claim:

1. A new and distinct strawberry plant named 'CBC005' as described and illustrated herein.

* * * * *